(12) United States Patent
Edwards et al.

(10) Patent No.: US 6,494,611 B2
(45) Date of Patent: Dec. 17, 2002

(54) APPARATUS FOR MIXING A LIQUID AND DRY POWDERED COMPONENTS

(75) Inventors: Brian Edwards, West Milford, NJ (US); Paul Higham, Ringwood, NJ (US); Joseph Zitelli, River Edge, NJ (US)

(73) Assignee: Howmedica Osteonics Corp., Allendale, NJ (US)

( * ) Notice: Subject to any disclaimer, the term of this patent is extended or adjusted under 35 U.S.C. 154(b) by 5 days.

(21) Appl. No.: 09/770,982

(22) Filed: Jan. 26, 2001

(65) Prior Publication Data

US 2002/0101784 A1 Aug. 1, 2002

(51) Int. Cl.$^7$ ................................................ B01F 11/00
(52) U.S. Cl. ........................ 366/209; 366/216; 366/218
(58) Field of Search .................................. 366/209, 216, 366/218, 116, 110, 210, 211, 212, 219, 237, 239, 240

(56) References Cited

U.S. PATENT DOCUMENTS

| | | | |
|---|---|---|---|
| 1,421,016 A | * 6/1922 | Leipold | |
| 1,489,024 A | * 4/1924 | Burnett | |
| 1,490,214 A | * 4/1924 | Johnson | |
| 1,686,135 A | * 10/1928 | Hurlde | |
| 2,151,123 A | * 3/1939 | Lavine | |
| 3,275,302 A | * 9/1966 | Horton | |
| 3,684,136 A | 8/1972 | Baumann | 222/386 |
| 3,739,947 A | 6/1973 | Baumann et al. | 222/136 |
| 3,749,371 A | * 7/1973 | Folkenroth et al. | |
| 3,756,571 A | 9/1973 | Winberg | 259/60 |
| 3,828,434 A | 8/1974 | Mosch | 32/60 |
| 3,831,742 A | 8/1974 | Gardella et al. | 206/219 |
| 3,917,062 A | 11/1975 | Winters | 206/219 |
| 4,084,320 A | 4/1978 | Skeirik | 32/60 |
| 4,523,855 A | * 6/1985 | Walker | |
| 4,551,135 A | 11/1985 | Gorman et al. | 604/82 |
| 4,555,183 A | 11/1985 | Thomas | 366/208 |
| 4,648,532 A | 3/1987 | Green | 222/82 |
| 4,787,751 A | * 11/1988 | Bakels | |
| RE33,161 E | 2/1990 | Brown et al. | 423/308 |
| RE33,221 E | 5/1990 | Brown et al. | 423/308 |
| 5,058,770 A | 10/1991 | Herold et al. | 222/80 |
| 5,088,830 A | * 2/1992 | Muhlbauer | |
| 5,100,241 A | 3/1992 | Chan | 366/139 |
| 5,114,240 A | 5/1992 | Kindt-Larsen et al. | 366/129 |
| 5,167,448 A | 12/1992 | Herold et al. | 366/213 |
| 5,184,893 A | * 2/1993 | Steele et al. | |
| 5,193,907 A | 3/1993 | Faccioli et al. | 366/130 |
| 5,336,264 A | 8/1994 | Constantz et al. | 623/16 |
| 5,395,167 A | 3/1995 | Murray | |
| 5,511,879 A | * 4/1996 | Fletcher | |
| 5,927,851 A | * 7/1999 | Carlson | |
| 5,971,599 A | * 10/1999 | Bothers | |
| 6,083,229 A | 7/2000 | Constantz et al. | 606/92 |
| 6,099,160 A | 8/2000 | Flackett | 366/217 |

FOREIGN PATENT DOCUMENTS

| | | |
|---|---|---|
| EP | 0 976 441 A1 | 2/2000 |
| FR | 2 572 677 | 9/1986 |

* cited by examiner

Primary Examiner—Tony G. Soohoo
(74) Attorney, Agent, or Firm—Lerner, David, Littenberg, Krumholz & Mentlik, LLP

(57) ABSTRACT

An apparatus for mixing dry and liquid components is used to form a setting paste. A holder is mounted on the apparatus for reciprocating movement with respect to a base of the apparatus. The movement has an amplitude with components in first and second perpendicular directions. A drive system is operatively connected to the holder for imparting said reciprocating movement to said holder at a predetermined number of cycles per minute. A container having a mass of said dry and liquid components therein is mounted in the holder. The mass, amplitude and cycles per minute of reciprocation being chosen to produce an energy input of at least about $3 \times 10^{-3}$ Joules per second per 3 cc of mixture.

28 Claims, 12 Drawing Sheets

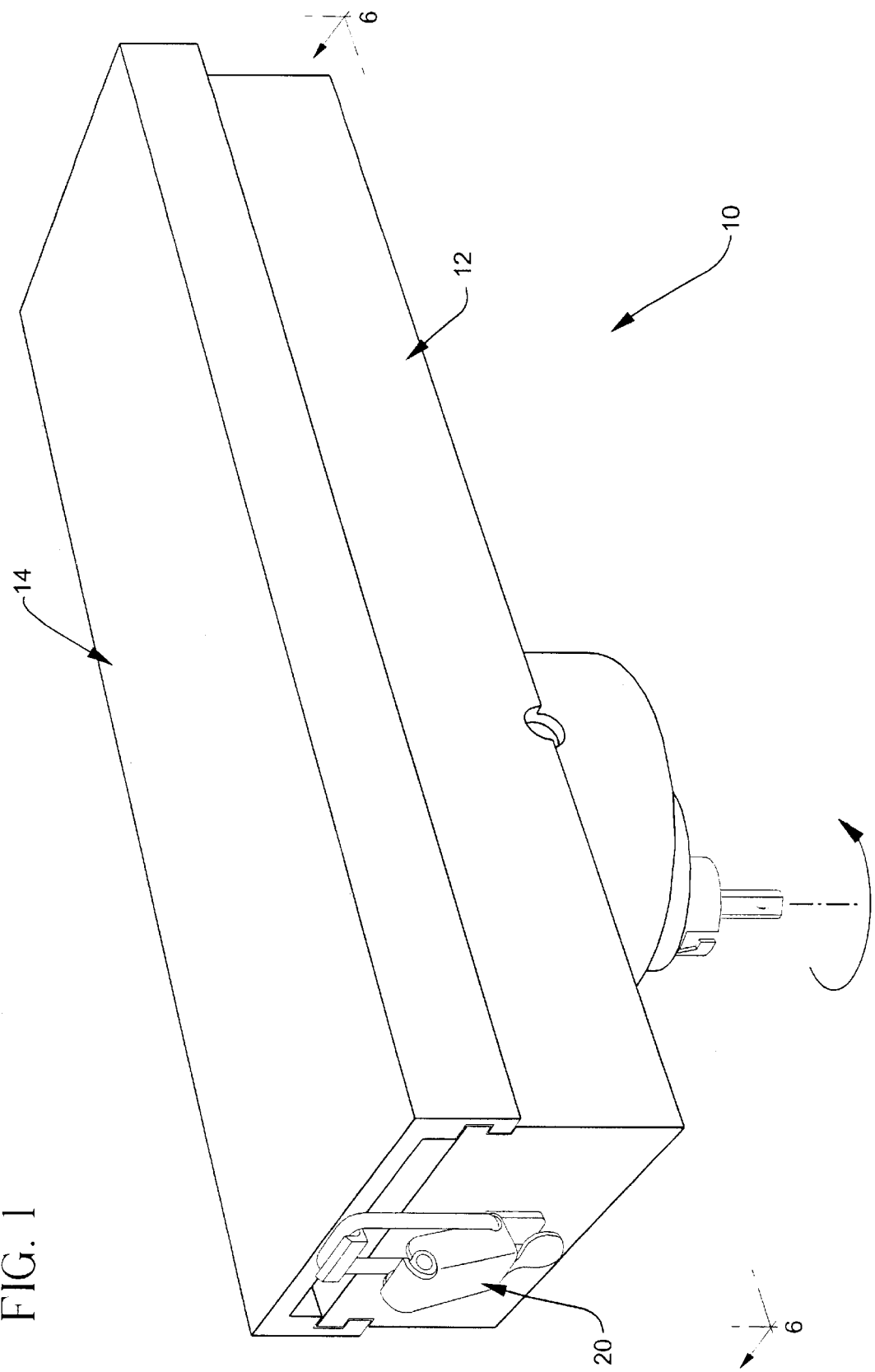

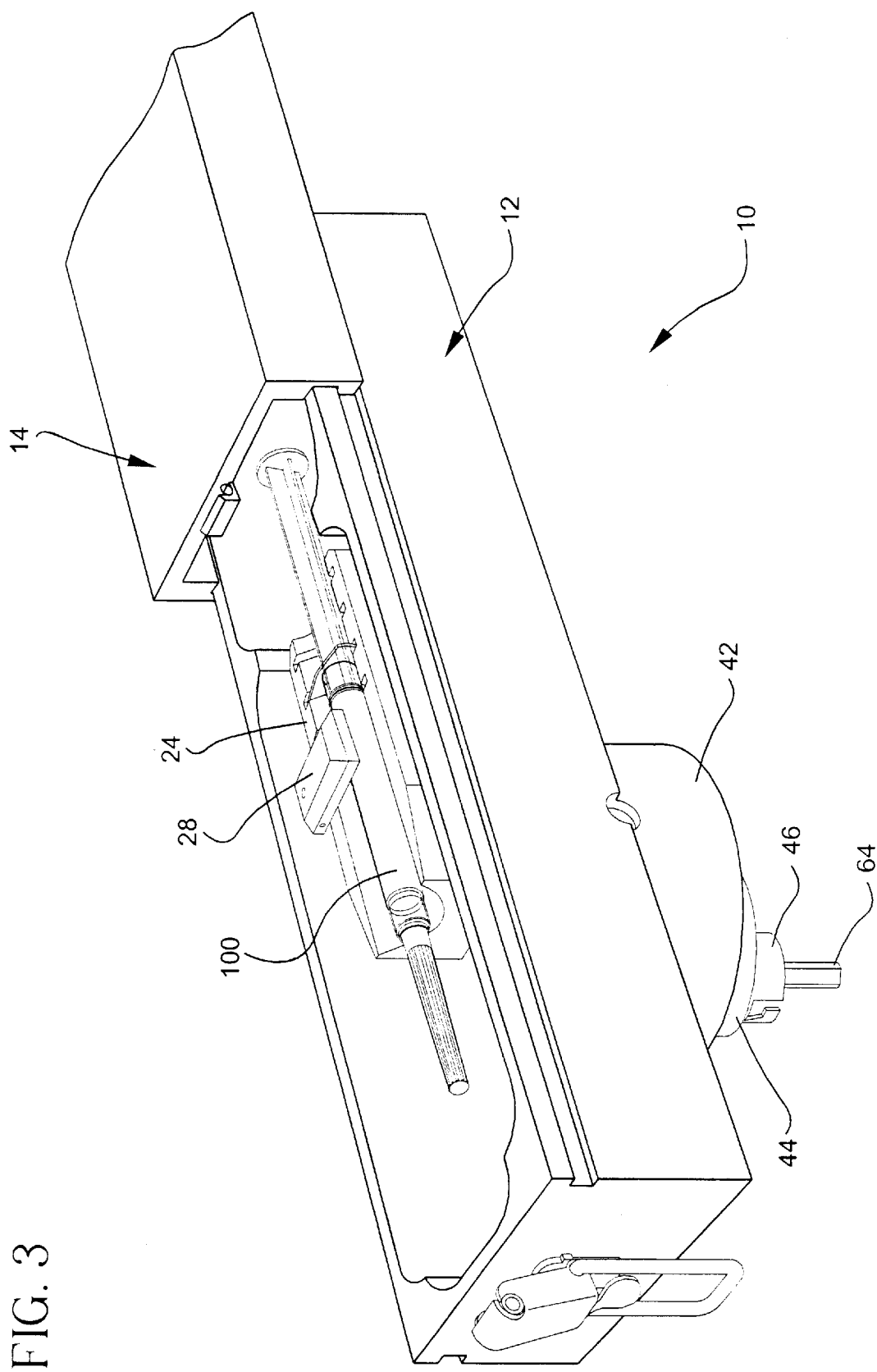

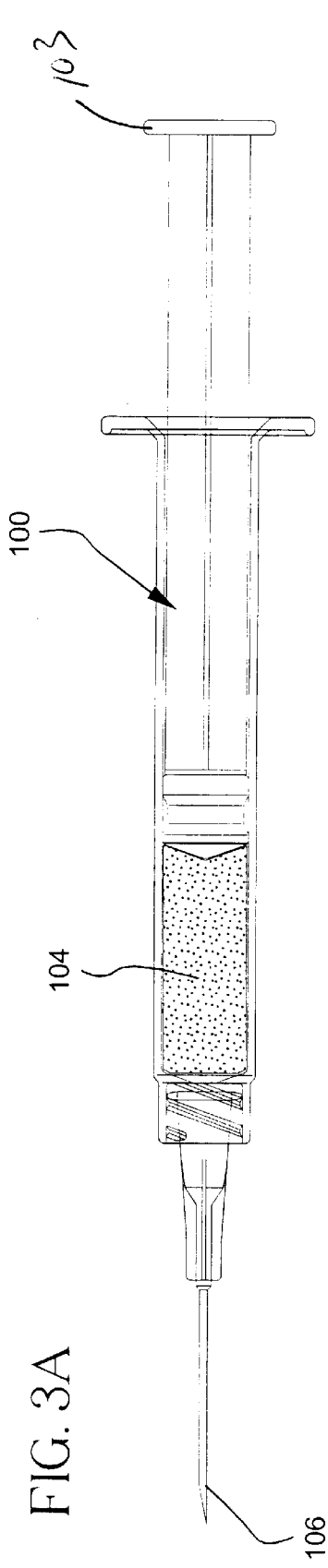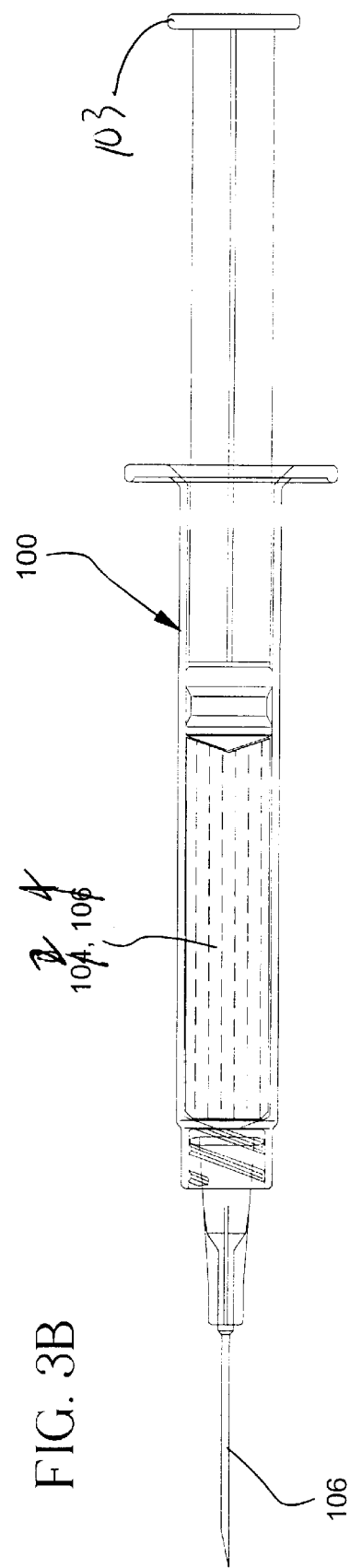
FIG. 3A
FIG. 3B

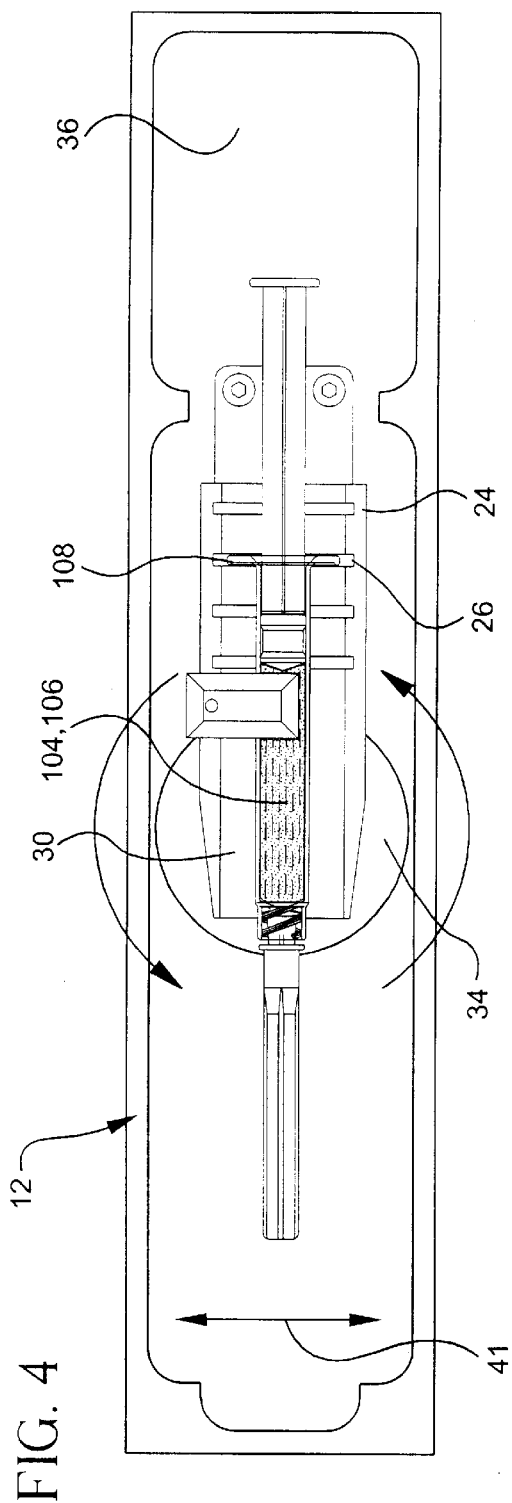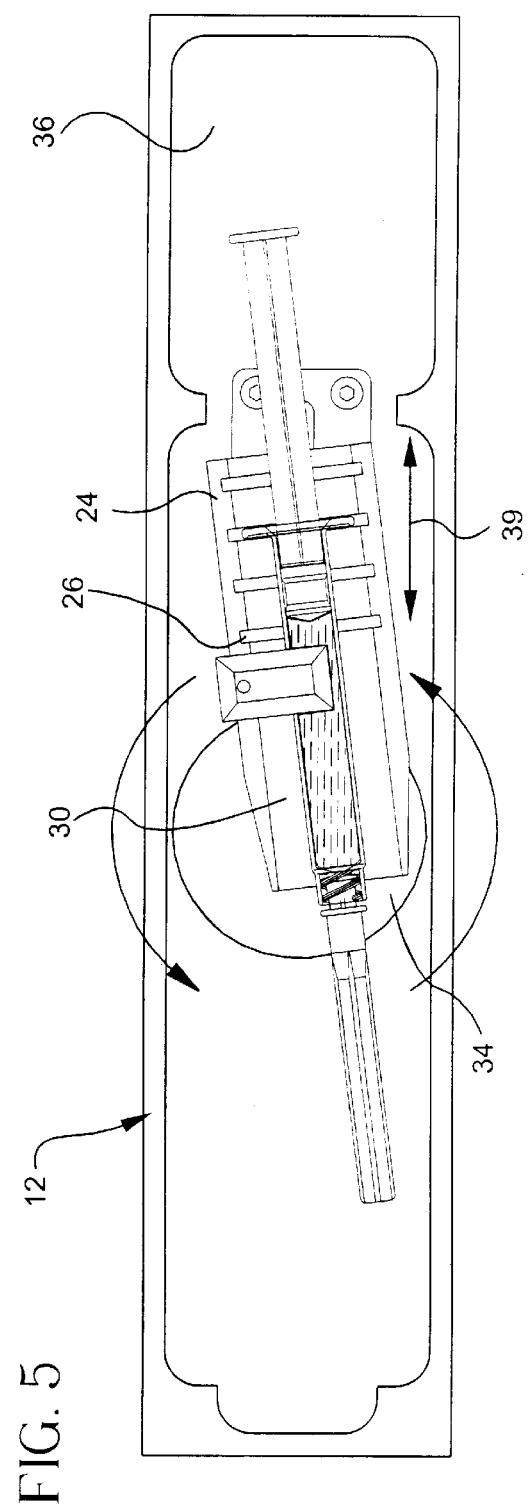

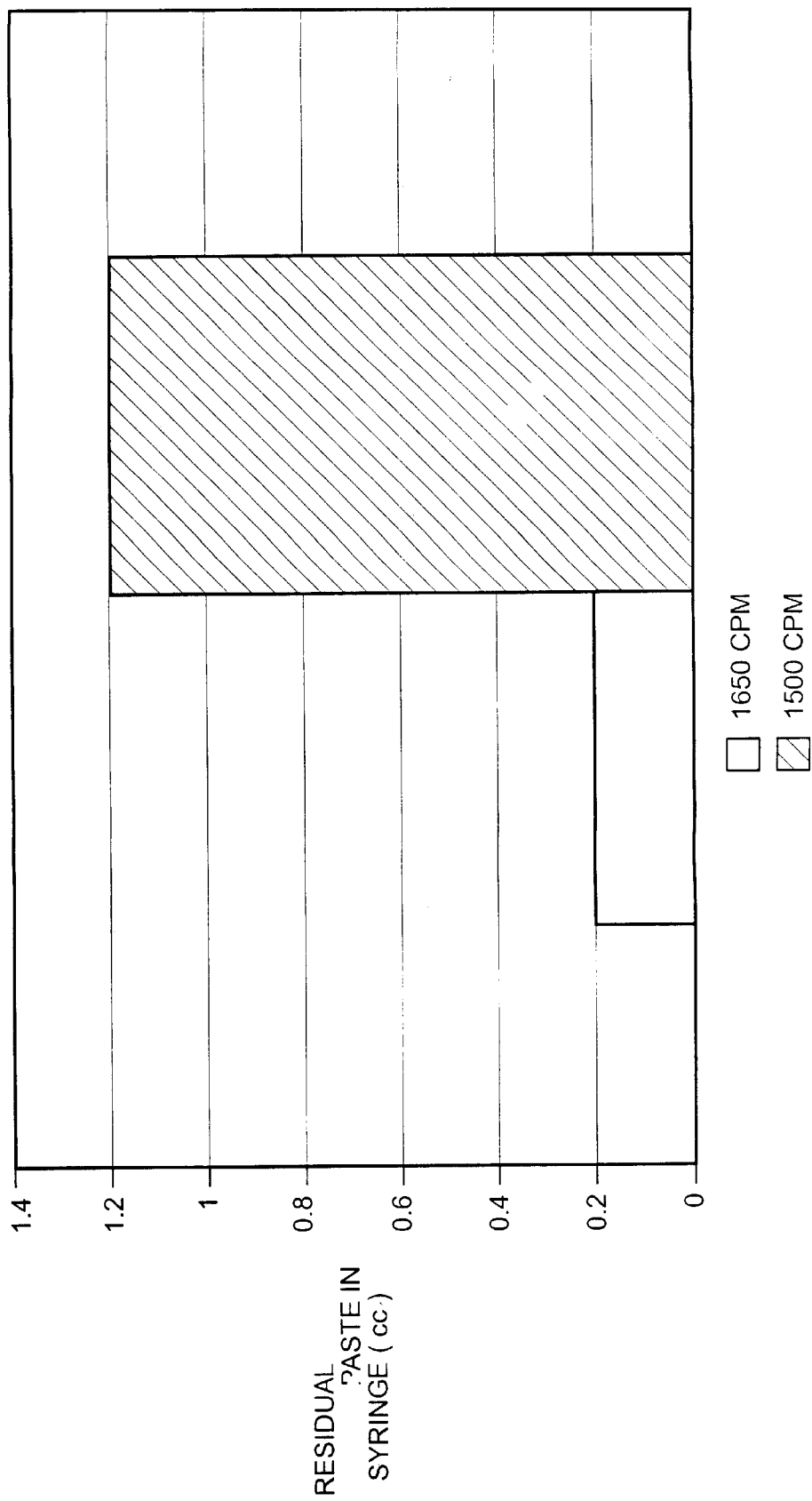

APPARATUS FOR MIXING A LIQUID AND DRY POWDERED COMPONENTS

BACKGROUND OF THE INVENTION

This invention relates to a mixing device for mixing bone cement comprised of a dry and a liquid component. More particularly, it relates to a bone cement made from mixing powdered calcium phosphate compounds and an aqueous setting solution.

Calcium phosphate cements for use in the operating room are currently mixed in a bowl with a spatula by hand. Either sterile water or a sterile 0.25M sodium phosphate solution (0.25M Na-phos) are used as the liquid component. Such cements are described in Brown and Chow U.S. Reissue Pat. Nos. 33,161 and 33,221 and Constantz et al. U.S. Pat. No. 5,336,264, the teachings of which are incorporated herein by reference. Optimally, mixing with water results in a faster setting time of 25 to 35 minutes, while mixing the 0.25M Na-phos solution results in a setting time of 5 to 8 minutes. These solutions are mixed with the calcium phosphate powders in a liquid to powder ratio of about 0.25 to 0.30 by weight.

The mixing of powder and liquid by hand with a spatula is a technique sensitive process since each individual mixing the cement performs the operation differently. To obtain optimal mixing the powder and liquid must be pressed against the side of the bowl and the mixture continuously spread and recombined during the mixing stage. Also, the time and amount of liquid for mixing is dependent on the operators perception of a good mixing consistency and is thus very subjective. Ideally 45 to 60 seconds of hand mixing is required but the hand mixing times vary widely from individual to individual. It has been found that these mixing techniques result in a wide variation in the physical properties of the hardened cement or bone filler because largely varying amounts of energy are inputted into the material during mixing. A desire to provide alternate delivery systems (i.e. by syringe needle or cannula) also necessitate that the mixed cement flow into and from a convenient dispenser. These factors have provided the impetus for the development of automatic mixing systems.

Applicants have found that when mixing calcium phosphate cements, in particular calcium phosphate cement made from powdered tetra-calcium phosphate and di-calcium phosphate in a 1:1 molar ratio which are mixed with water or other aqueous solutions, such as those containing sodium phosphates, that a high degree of wetting of each of the powder particles is necessary for the material to harden from a paste into a cement or bone filler having optimum physical properties. Although mixing devices existed in the prior art for combining powdered and liquid components, such were not used with calcium phosphate bone cements but rather these cements were hand mixed or mixed via methods which only inputted a low amount of energy into the mixing. Such a low energy mixing system is disclosed in U.S. Pat. No. 6,083,229.

A typical prior art dental mixer is shown in FIG. 1A is used to make dental amalgams and has an almost linear motion with a travel distance of about 1.6 cm in each direction. The complete cycle (a back and forth eccentric motion) has a total travel distance of 3.2 cm. The side to side motion per cycle is about 0.5 cm. The motor runs at 3290 rpm and produces one back and forth motion each rotation or 3290 cycles per minute. However, the motor is of low power and can only mix less than one gram of material.

Another mixer is made by Ivoclar which has a two pivot point eccentric motion with 2.8 cm of linear travel and 5 cm of up and down motion at one end. This system runs at a fixed 1788 rpm.

When a syringe containing a powdered calcium phosphate mineral and an aqueous solution is affixed to the prior art mixing apparatus of FIG. 1A, an intimate powder-liquid mixture results having a high degree of wetting. This mixing is superior to hand mixing. Such an improvement in wetting is shown by the ability to eject the paste through an 18 gauge or larger needle.

While this system can be modified to meet the mixing energy input and motion requirements for forming a calcium phosphate paste which can be injected, its mixing motion is not optimal and it is not a system suitable for hospital or operating room use for sterilization reasons. The mixer of the present invention can hold a large container, similar in volume to a 60 cc syringe. In its preferred embodiment, one complete cycle in this system has 3.2 cm of linear travel. There is also a maximum of 3.5 cm up and down motion on one end of the tubular syringe and a variable amount of up and down motion along the longitudinal extent of the rest of the mixing chamber.

The system of the present invention has the capability of reciprocating a container in an eccentric motion at between 800 to 2000 cycles per minute (cpm) and provides sufficient energy to form a paste which can be ejected through an 18 gauge or larger needle. The system of the present invention is a well-balanced system which minimizes vibration by means of a counter weight on the drive plate, providing a very smooth motion at high cycles per minute. This system meets the mixing energy input and motion requirements for forming a calcium phosphate paste which can be injected and may be made sterilizeable. The calcium phosphate powder may be packaged after sterilization so that sterile liquid can be added to the powder and the two components mixed together, while in a sterile package such as a syringe. Alternatively the syringe and powder combination can be sterilized together.

SUMMARY OF THE INVENTION

It is an object of this invention to provide a mixing device for mixing dry and liquid components.

It an additional object of this invention for providing a mixing device for mixing dry calcium phosphate powders and aqueous solutions which provides a high degree of coating of the dry powders with the aqueous solution.

It is yet an additional object of the invention to provide a mixing device which inputs a predetermined mixing energy into the mixture over a predetermined time in order to effect the complete wetting of the dry powders with the aqueous solution.

These and other objects are accomplished by a mixing apparatus for mixing dry and liquid components to form a paste which has a holder mounted on the apparatus. The holder is mounted for eccentric reciprocating movement of a predetermined up and down and side to side amplitude. The movement has components in at least two perpendicular directions. A drive system is operatively connected to the holder for imparting the reciprocating movement to the holder at an optimal number of cycles per minute depending on the materials to be mixed. Initially a container having a mass of dry and liquid components therein are mounted in the holder.

The mass, amplitude and cycles per minute of reciprocation are chosen to produce an energy input of at least about $3 \times 10^{-3}$ Joules/second. The drive system is capable of driving the holder in the reciprocating motion at least about 1600 cycles per minute. The reciprocating movement occurs in a plane with the first and second directions of movement being perpendicular along said plane. The drive system includes an input shaft rotating a drive plate with the plate having the holder pivotally mounted thereon at a first pivot point with an axis offset from an axis of the input shaft to impart an eccentric motion to the holder as said drive plate rotates about the input axis. The holder has a first end coupled to the offset first pivot point and a second end pivotally mounted on the apparatus at a second pivot point in a manner permitting a first amplitude of movement in the first direction along said plate and permitting a lower amplitude movement in the second direction along the plate.

The mixing apparatus includes a base having a circular drive plate mounted thereon with the input shaft rotating the drive plate about its central axis with the holder mounted at a first pivot point radially spaced from the central axis of the plate. The holder second pivot point is spaced along the holder from the first pivot point along the first direction. The second pivot includes a pin slidably mounted in a longitudinal slot in the base of the mixer with the slot extending in the first direction. The container is removably mounted in the holder and may be in the form of a sterile syringe pre-packaged with the dry component. The liquid component, such as a sterile aqueous solution, is brought into the syringe immediately before use by activating the plunger of a standard syringe to draw the liquid into the syringe barrel. Alternatively, both the powder and the liquid component may be added to the syringe immediately prior to mixing.

The dry component may comprise a calcium phosphate mineral powder such as a combination of tetra-calcium phosphate and di-calcium phosphate and the liquid component may be an aqueous solution of either sterile de-ionized water or a sterile water and sodium phosphate solution. The dry component also may include dry sodium phosphate particles. The liquid powder ratio in the syringe prior to mixing is generally between 0.25 and 0.3. The syringe should have an excess of empty volume of approximately 1 cc after it has been loosely filled with the powder. Addition of the liquid component will consolidate and decrease the volume of the loosely packed powder.

These and other objects and advantages of the present invention will become apparent from the following description of the accompanying drawings, which disclose several embodiments of the invention. It is to be understood that the drawings are to be used for the purposes of illustration only and not as a definition of the invention.

BRIEF DESCRIPTION OF THE DRAWINGS

In the drawings wherein similar reference characters denote similar elements throughout the several views, in which:

FIG. 1 is an isometric view of the mixing unit of the present invention mounted within a case;

FIG. 3 shows the case of FIG. 2 with the holder mounted therein and the container for the powdered and liquid component in the form of a syringe mounted on the holder;

FIG. 3A is an elevation view of the syringe loaded with dry calcium phosphate powder;

FIG. 3B is an elevation view of the syringe after an aqueous solution is drawn into or added to the barrel thereof and mixed with the dry powder component;

FIG. 4 is a plan view of the open case of FIG. 3 with the container therein mounted in the holder with the arrows indicating the reciprocating movement of the holder within the case;

FIG. 5 is a plan view similar to that of FIG. 4 showing the holder and container, in the form of a syringe, in a position displaced from that of FIG. 4 during the reciprocation process;

FIG. 11 represents the residual paste in the apparatus of FIG. 7 using the mixing apparatus of the present invention with the left hand graph representing mixing speed of 1650 cpm and the right hand graph representing mixing at 1500 cpm.

DESCRIPTION OF THE PREFERRED EMBODIMENTS

Figure 1A:
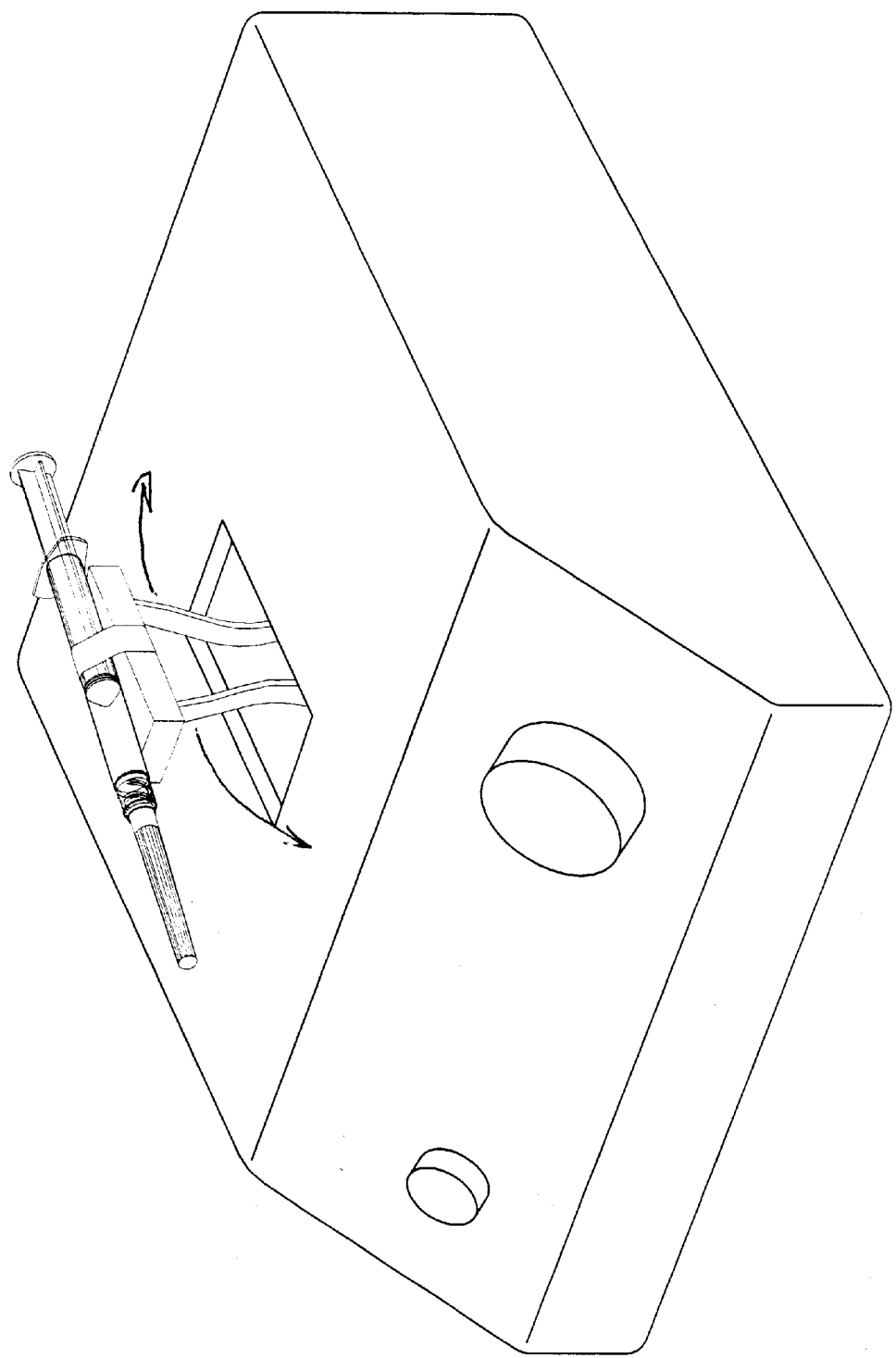
FIG. 1A is an isometric view of a prior art mixing system.
Figure 2:
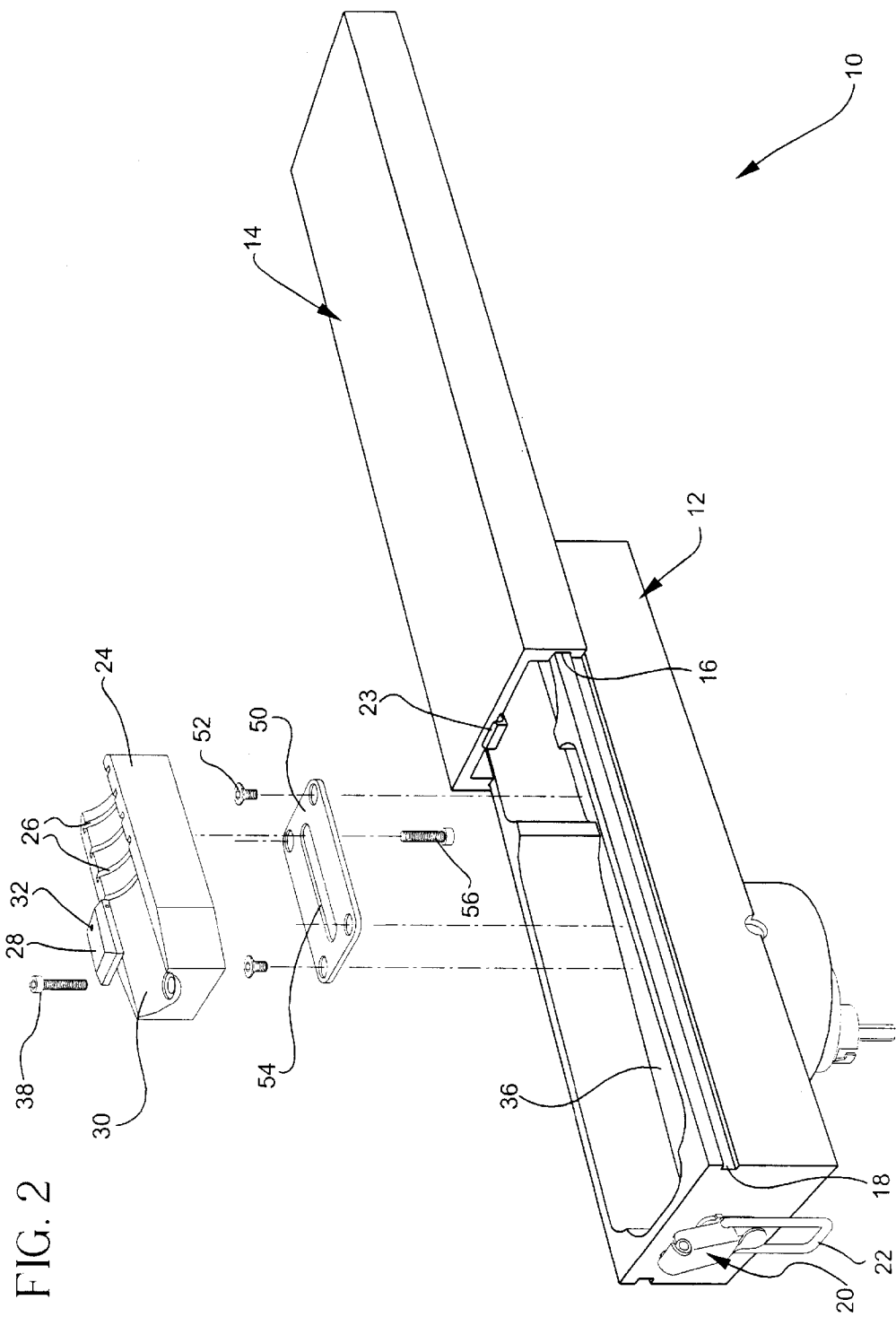
FIG. 2 is a partially exploded isometric view of the case in FIG. 1 with the lid thereof partially open with the holder for the container having the liquid and powdered components therein being shown detached from the interior of the mixing case.

Referring to FIGS. 1 to 3, there is shown a mixing apparatus generally denoted as 10 which includes a bottom or base portion 12 and a lid portion 14. Apparatus 10 allows the high speed mixing of a container holding a powder and a liquid. FIG. 1A shows a prior art mixer in which dental amalgams are mixed. This mixer produces a back and forth and side to side motion.

In the preferred embodiment, lid 14 includes a pair of slots or grooves 16 which slidably engage a pair of rails 18 adjacent the open end 19 of base 12. Apparatus 10 includes a locking mechanism generally denoted as 20, which, in the preferred embodiment, is in the form of a latch having an arm 22 mounted on base 12 which engages a complimentary latch element 23 on lid 14. Thus, apparatus 10 may be selectively opened and closed by unlocking latch 20 and sliding lid 14 relative to base 12. Mounted within the interior of base 12 is a holder 24 which, in the preferred embodiment, is designed to receive a syringe 100 containing the powdered and liquid components which may be the calcium phosphate cements taught in U.S. Re 33,161.

Holder 24 has a series of grooves 26 and a concave surface 30 for this purpose. The preferred syringe has about 20 cc in usable volume and holds up to approximately 20 g of calcium phosphate powder which occupies about 90% of the volume. In one embodiment the syringe is pre-filled with powder and sterilized prior to being supplied to the user. Alternately, the syringe is filled with sterilized powder prior to mixing.

Referring to FIG. 3A there is shown the syringe 100 filled with powder either as supplied by the manufacture with the desired amount of dry powder 104 pre-packaged therein or filled in the operating room. Referring to FIG. 3B, there is shown the preferred syringe 100 containing the liquid component 102 and the powdered component 104. To fill syringe 100 with liquid the user either draws the required liquid component into the syringe through its needle or tip 106 by moving plunger 103 or may place the liquid in the syringe barrel after placing the powder therein. Liquid 102 may be provided in any suitable container (not shown) or, if water, may be taken from any convenient sterile source. In the preferred embodiment, the powder is a calcium phosphate powder and the liquid is an aqueous solution which may contain water and other components such as sodium phosphate in solution.

The preferred syringe 100 includes a flange 108 which is designed to be received within one of the complimentary series of grooves 26 along concave surface 30 in holder 24. The engagement between flange 108 and grooves 26 in holder 24 ensures that the body 101 of syringe 100 is prevented from longitudinal axial motion with respect to the holder during the reciprocation thereof.

In the preferred embodiment, holder 24 includes a series of grooves 26 so that syringe 100 may be located in different positions with respect to the longitudinal extent of holder 24. In the preferred holder there are four grooves 26 spaced about 10 mm apart.

The preferred holder 24 includes a clamping arm 28 which can move into and out of engagement with the outer diameter of syringe body 101 by rotation about a pivot pin 32 while the flange 108 is held within a groove 26 of holder 24. Any other method of retaining syringe 100 in holder 24 during mixing would be acceptable.

Referring to FIGS. 4 and 5, a plan view of holder 24 is shown with flange 108 placed in the second of four grooves 26 formed on concave surface 30 of holder 24. The syringe barrel 101 is received within concave seating surface 30 of holder 24 and held therein by clamping arm 28 which is pivoted about pin 32 from an open position to a closed position where it engages the outwardly facing cylindrical surface of syringe barrel 101.

Figure 6:
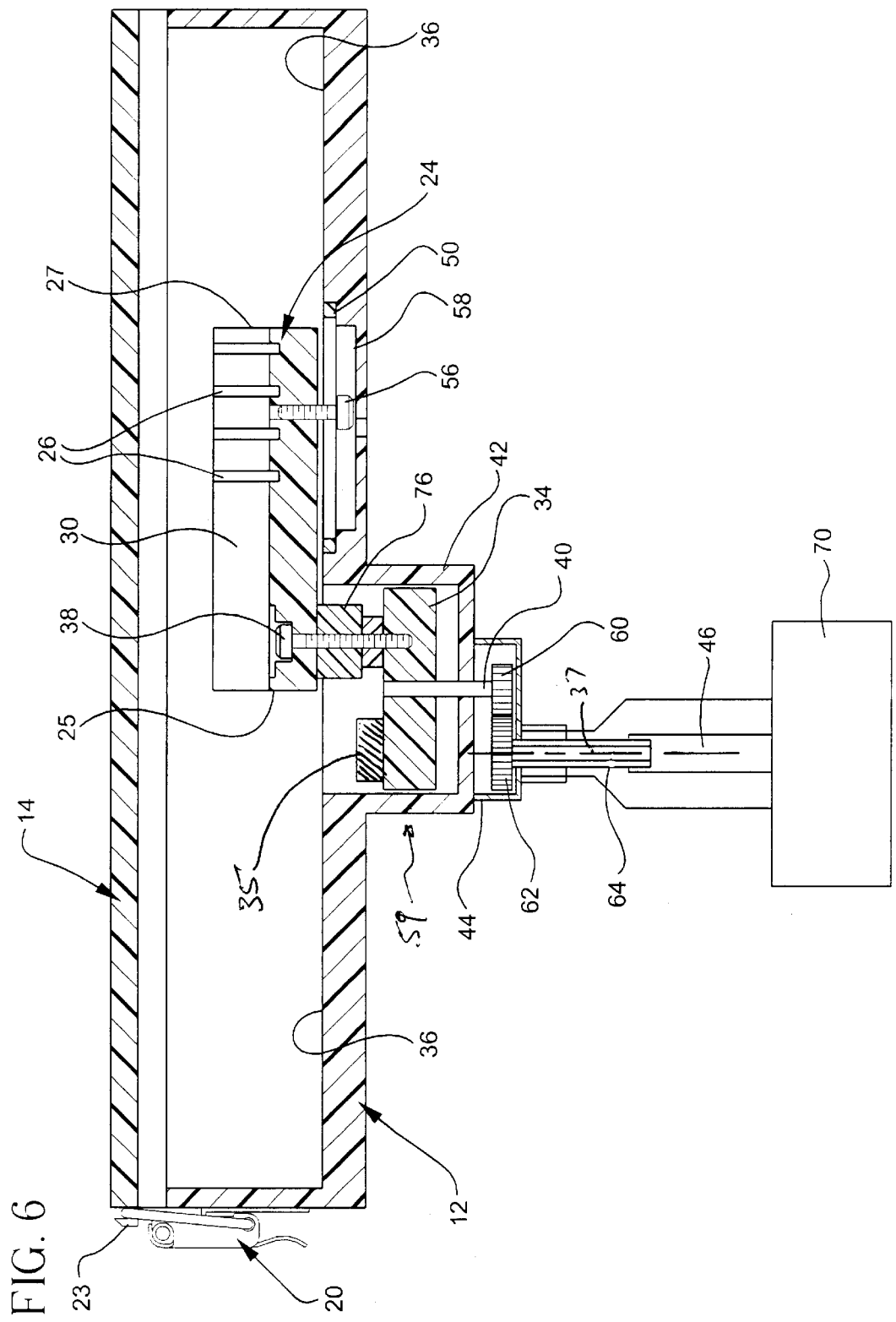
FIG. 6 is a cross-sectional view along the lines 6—6 of FIG. 1 showing the drive system for reciprocating the holder of the present invention.

Referring to FIGS. 2 and 6, there is shown the preferred mounting of holder 24 within a base 12. Holder 24 is mounted on a circular rotating plate 34 mounted in or adjacent the bottom surface 36 of base 12. Plate 34 is mounted so that it may rotate with respect to base 12 about a central axis 37. As can be best seen in FIG. 6, holder 24 is pivotally mounted on plate 34 by a pin or screw 38 mounted flush with or below concave surface 30. Pivot pin or screw 38 defines an offset pivot axis about which holder 24 may rotate as plate 34 rotates about its central input axis 37. Since the head of screw or pin 38 is recessed or flush, it does not interfere with the placement of syringe barrel 101 on concave surface 30. In order to maintain a smooth motion of plate 34 a counterweight 35 is used to balance the effect of holder 24 and thereby reduces vibration.

In the preferred embodiment, plate 34 is circular and includes a central drive shaft 40. Shaft 40 rotates plate 34 and thereby causes the circular reciprocating motion of holder 24 about the offset axis 37 of pin 38. The movement has components of motion in two directions 39 and 41. With respect to FIGS. 4 and 5 direction 41 is up and down and direction 39 is back and forth. The back and forth amplitude at pin 38 in direction 39 is equal to twice the distance A from the center line of drive shaft 40 to the center line of the offset axis of pin or screw 38. In the preferred embodiment A is 1.6 cm. Likewise, the up and down motion in direction 41 of FIG. 4 at pin 38 has a total amplitude of 3.2 cm. The up and down amplitude varies at various points along the longitudinal extent of syringe 100 depending on the distance therealong from the offset axis of pin 38.

As best seen in FIG. 2, a slotted plate 50 is fixably attached to bottom surface 36 of base 12 by, in the preferred embodiment, four screws 52. Plate 50 includes a slot 54 which extends longitudinally along the first direction 39 of base 12. Holder 24 is mounted for sliding movement in slot 54 on plate 50 by a pivot screw or pin 56 mounted upwardly through plate 50 and into holder 24 with respect to base 12. A recessed area 58 is formed in base bottom surface 36 so that the head of the screw 56, which is larger than the width of slot 54, may move with respect to base 12 in the longitudinal direction 39. The amplitude of this movement in direction 39 is again twice the distance A as described above.

Since slot 54 of plate 50 prevents up and down movement of pivot pin 56 in direction 41 as shown in FIGS. 4 and 5, the amplitude of motion of end 27 of holder 24 in the up and down direction 41 is limited by the engagement of pin or screw 56 within slot 54. Thus, the up and down amplitude of holder 24 at pin or screw 56 is essentially zero. However, the up and down amplitude increases on moving in direction 39 away from pin 56 in either direction. In the preferred embodiment the maximum up and down amplitude is 1.6 cm in each direction. Because there are two pivot points provided by pin or screw 38 and pin or screw 56 an eccentric mixing motion which imparts a sufficient amount of energy into the powder and liquid to ensure the substantially complete wetting of the powdered component 104 and liquid 102 is achieved. The amplitude of up and down motion of the syringe 100 may be varied by placing flange 108 of syringe 100 in different grooves 26 along the longitudinal extent of holder 24.

In the preferred embodiment, the rotating plate 34 is driven by a gear system 59 composed of a first gear 60 driving input shaft 40 and a second gear 62 being driven by a drive shaft 64. In the preferred embodiment, the gear ratio between gear 62 and gear 60 is 1:2. Thus, for each rotation of shaft 64, shaft 40 and therefore plate 34 rotates two times. Shaft 64 may be driven by any convenient method which, in the preferred embodiment, it is a reamer or a drill driven at a constant speed by an electronic control system which provides power to the drill. This is shown in FIG. 6 as black box 70 which includes the power control system and the drive motor (not shown). In the preferred embodiment, the system 70 used to drive shaft 64 is a Stryker Instruments TPS MicroDriver power source which source is connected to standard available power (110 or 220 volts) and drives a Stryker 2104 reamer at a constant speed of at least 800 rpm which is stepped up by the 2:1 gear ratio of the preferred gear system 59 to at least 1600 cycles per minute. In an alternate embodiment a battery pack may be used as a power supply. These devices may be obtained from Stryker Instruments of Kalamazoo, Mich.

Referring to FIG. 3, there is shown mixer 10 with lid 14 in the open position showing the interior of base 12. Syringe 100 is located in holder 24 and held therein by clamp 28. Base 12 includes a recessed portion 42 which, as shown in FIG. 6, houses rotating plate 34. Recess 42 includes a gear box extension 44 which houses gear 60 and 62 of gear system 59. An adapter 46 is provided around shaft 64, which adapter in the preferred embodiment, is designed to mate with the drive head of a drill or drive unit (not shown). The connection between shaft 64 and the drive system may be accomplished in any one of a number of convenient manners such as a standard drill chuck. Since holder 24 is mounted above bottom surface 36 of base 12 spacers 76 are used to rigidly connect plate 34 and holder 24 via pin 38.

EXAMPLE 1

The mixing apparatus 10, as shown in FIGS. 1–6 was used to mix a calcium phosphate powder comprising tetra-calcium phosphate and di-calcium phosphate and an aqueous solution. The powder had particles of approximately 0.1–15 micrometers in size. A Stryker 2104 Reamer Drill (not shown) also available from Stryker Instruments of Kalamazoo, Mich., with a variable speed trigger (similar to a standard variable speed and drill) was powered by a 2115 Nickel-Cadmium Battery pack and was used as the drive system for driving the input shaft 64 of mixing machine 10. An adapter key or chuck on the reamer drives input shaft 64, which in the preferred embodiment, is coupled to a gear box, which gear box increases the rpm by a factor of 5. The higher gear ratio was required since the battery pack supplies relatively low power. The gear box drove shaft 40 coupled to mix head 34. The mix head moved the syringe in the two pivot point reciprocating motion described above. There was about 3.2 cm of linear motion and a variable amount (maximum of 3.5 cm) of up and down motion of the mixer head (see FIG. 5). As indicated above, the amount of up and down motion depended on the position of the material along the longitudinal axis of the syringe in relation to the two pivot points. The magnitude of the up and down motion can be varied by locating flange 108 of syringe 100 in different locations of slot 26 on holder 24.

The reamer or drill had a maximum rpm of about 330, which, with the 1:5 gearing, results in a maximum mixing head rate of about 1650 cpm.

The advantage of this embodiment is that the drive system and battery packs are sterilizable as are the mix head and gearbox which are autoclavable and are currently used in operating rooms. However speed was difficult to maintain since as the batteries drained the output speed of the drill dropped. Thus, a constant power source is preferred.

EXAMPLE 2

A mixing system using Stryker Instruments TPS Micro-Driver as the power source (available from Stryker Instruments of Kalamazoo, Mich.) was connected to the mixing apparatus of the present invention via a MicroDriver drill. The TPS power source has a power console, which is powered by connecting it to a 110V outlet (a 220V option is available). The console controls the speed of a variable MicroDriver drill (0–1000 rpm output), also available from Stryker Instruments. The drill head was connected to input shaft 64 and its motor was connected to the TPS power source by a power cord. Since the 110 volt power source did not vary the power to the drill, the speed could be maintained constant for long periods of time. The preferred drill is sterilizable.

Mixing apparatus 10 was also attached to this drive system via input shaft 64. A 20 cc syringe containing 10 cc of powder and 2.5 cc of liquid was clamped in the holder 24 and was put through the two pivot point mixing motion described above. The back and forth linear travel in the first direction during a cycle was 3.2 cm, while the up and down motion in the second direction again varied with the syringe position along holder 24 longitudinal the axis, reached a maximum of about 3.5 cm. The mixing chamber shaft 64 was slid into the MicroDriver drill handle, and locks into place in the same manner as a standard drill attachment. The TPS control system has a digital readout of the rpm driving the mixing chamber, but it has a maximum rate of only 1000 rpm which required the gear box, in the preferred embodiment, to be stepped up to the desired drive speed for the holder of the at least 1600 cycles per minute with the drill at 800 rpm or higher (approximately a 1:2 gear ratio). A typical duration of mix is 30 seconds.

The calcium phosphate powder was mixed with either sterile water or sterile sodium phosphate (Na-Phos) solution up to 0.25 Molar. The liquid phase was added at a ratio of liquid to powder (L:P) of about 0.25 to 0.30. These aqueous solutions had extremely low levels of dissolved solids and other ions.

Various tests were performed with 0.25M Na-phos and revealed that both the systems of Examples 1 and 2 successfully mixed the powder and liquid components together. After mixing, the 0.25M Na-phos solution the cement rapidly sets and a larger opening at the syringe tip 106 than 18 gauge end may be required to deliver the mixture.

For mixing with sterile water, both a L:P ratio of 0.25 and 0.3 was used. The higher ratio gave a more fluid mix and is easier to deliver through a syringe and even small gauge needles. For testing of mixing chamber oscillation speeds the L:P of 0.3 was used.

Changes in the rotation speed of the drive system effects all of the mixing systems in a similar manner. If the speed is not sufficient the calcium phosphate was not sufficiently wetted by the liquid component. Incomplete wetting during mixing results in the paste not being at its minimum viscosity, and will not have the best possible flow properties. Only with optimal flow properties will the calcium phosphate paste be injectable from a syringe.

Figure 7:
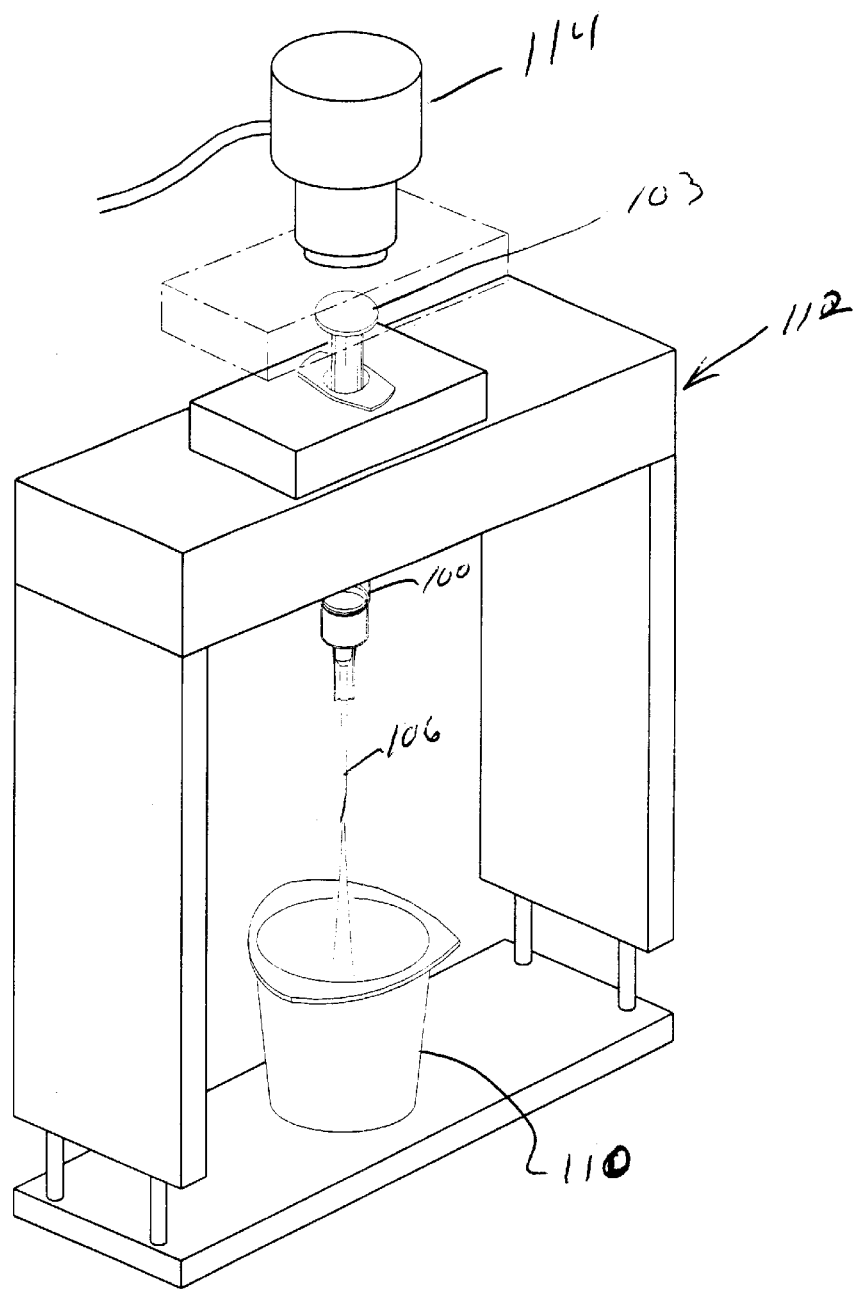
FIG. 7 is an isometric view of the test apparatus used to determine the flowability of the mixed calcium phosphate bone cement immediately after mixing with the apparatus of the present invention.

A series of mixing tests were run with sterile water as the aqueous solution at a L:P of 0.3. Three (3) grams of the calcium phosphate powder (tetra-calcium and di-calcium phosphate) was placed in a 10 cc syringe and 0.9 ml of liquid was added. The syringe was secured in the mixing apparatus 10 and driven by the drive system of Example 2, and typically mixed for 30 seconds, at between 1300 and 1750 cycles per minute (cpm). After mixing, the syringe plunger was pressed to the 3 cc level, while air is released from the syringe. The syringe 100 was then placed in a fixture above a cup 110 on a load frame shown generally denoted as 112 in FIG. 7. Load was applied to the plunger 103 of syringe 100 by a solenoid 114 in a manner consistent with delivery by thumb pressure, and the test terminated when the predetermined load of 30 lb. was exceeded. This load was chosen as an empirically determined approximation of a practical limit for a typical thumb force. Several different delivery tip configurations were evaluated. They included no tip (just out of the luer fitting opening diameter of 0.071"), a ½ inch 14 gauge dispensing needle, and a 1½ inch 18 gauge needle. The 18 gauge needle was used as the baseline for comparison of the various mix chamber oscillation speeds, since it was the most severe and discriminating test (smallest diameter).

Figure 8:
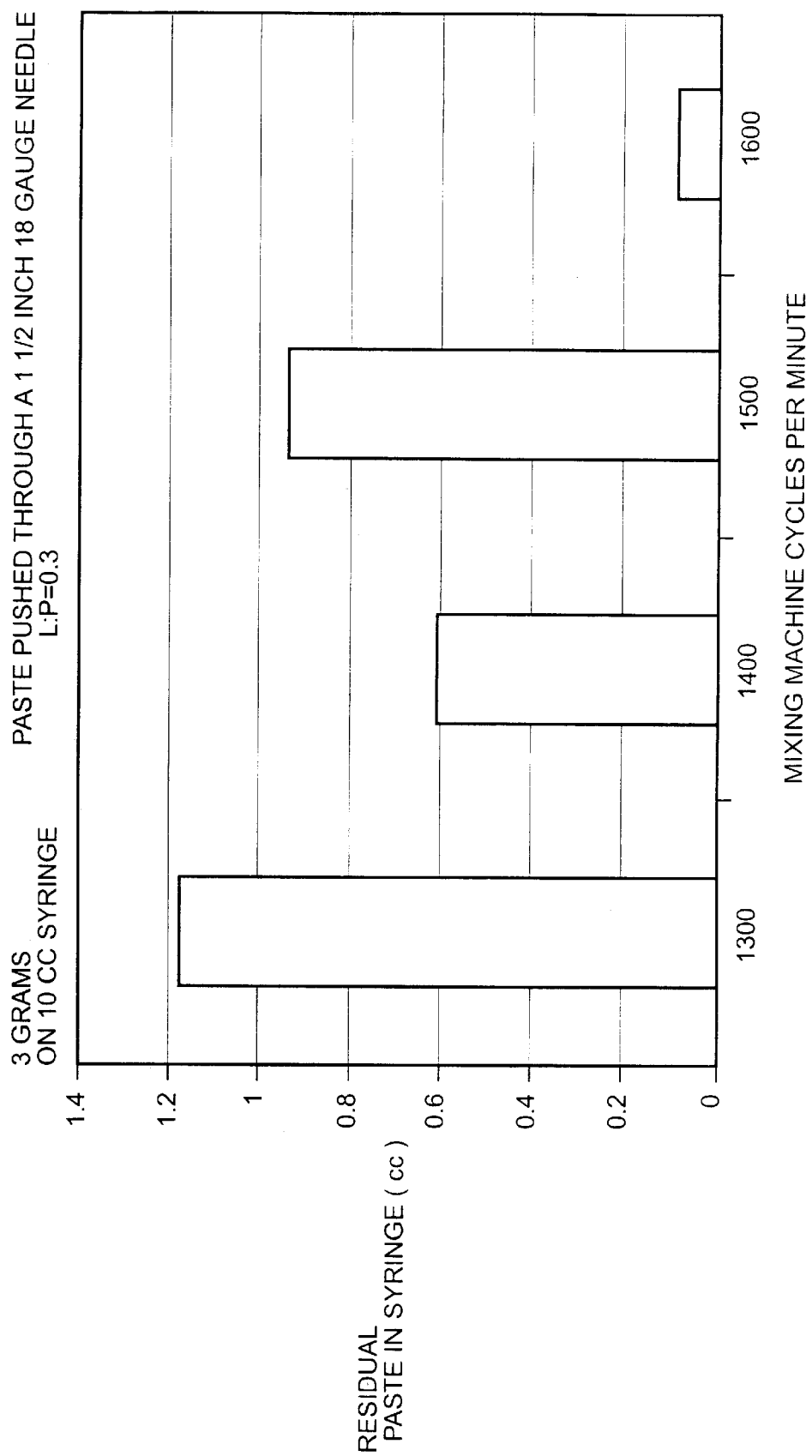
FIG. 8 is a graph showing the residual calcium phosphate paste remaining in the syringe in the test apparatus of FIG. 7 with the y-axis representing cubic centimeters of residual paste based on 3 grams of starting material pushed through a 1½-inch 18 gauge needle from a 10 cubic centimeter syringe with the x-scale representing a mixing speed of 1300, 1400, 1500 and 1600 respectively.

Using the apparatus 10 with its two pivot point mixing motion, a series of tests were run at 1300, 1400, 1500 and 1600 cpm. The volume of residual paste in the syringe barrel after the predetermined maximum plunger load of 30 lb. was reached was the evaluation criteria. The initial volume of mixed cement in the syringe was approximately 2 cc. The smaller the volume of paste not capable of passing through the 1½ inch 18 gauge needle and remaining in the syringe, the more successful the mixing at that cpm. The results are shown in FIG. 8 with the cubic centimeters of paste remaining on the vertical y-axis and the mixing cycles per minute (CPM) along the horizontal axis. All data is an average of at least there tests at each speed (n=3).

Figure 9:
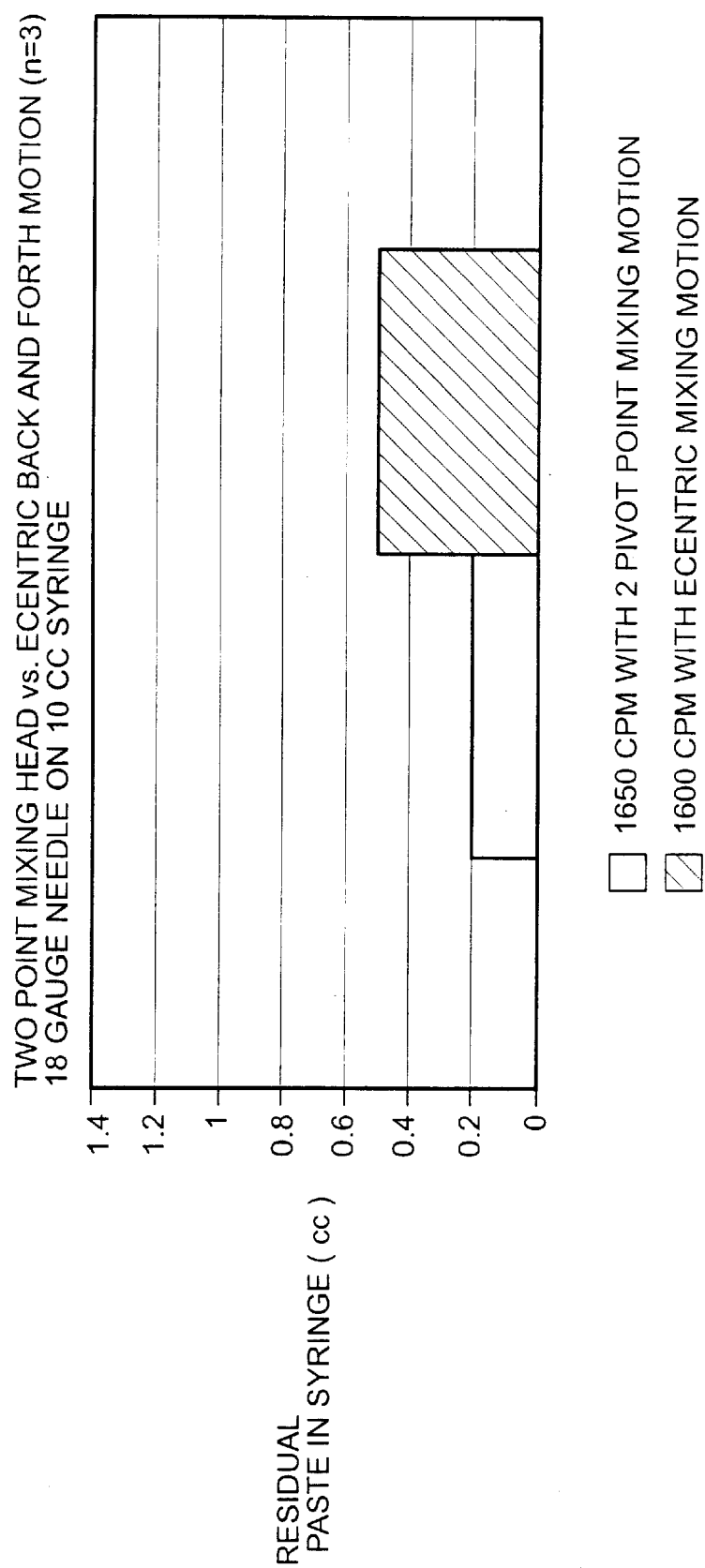
FIG. 9 shows the residual paste in the test apparatus of FIG. 7 on mixing with a 2 pivot point eccentric mixing motion of the present invention as shown in FIG. 1 at 1650 rpm on the left hand side of the x-axis and 1600 cpm utilizing the motion of the mixing machine of FIG. 1A.

These tests show a minimum of about 1600 cycles per minute are required to get sufficient mixing to expel at least 90% of the paste from the syringe with an 18 gauge needle. This is a result seen across the variety of mixing motions. Slower rates result in less flow and less consistent flow out of the syringe. As shown in FIG. 9, which has the same vertical y-scale as FIG. 8 and compares the two pivot point eccentric motion of the present invention at 1650 cycles per minute to the back and forth motion of the machine of FIG. 1A at 1600 cycles per minute.

Figure 10:
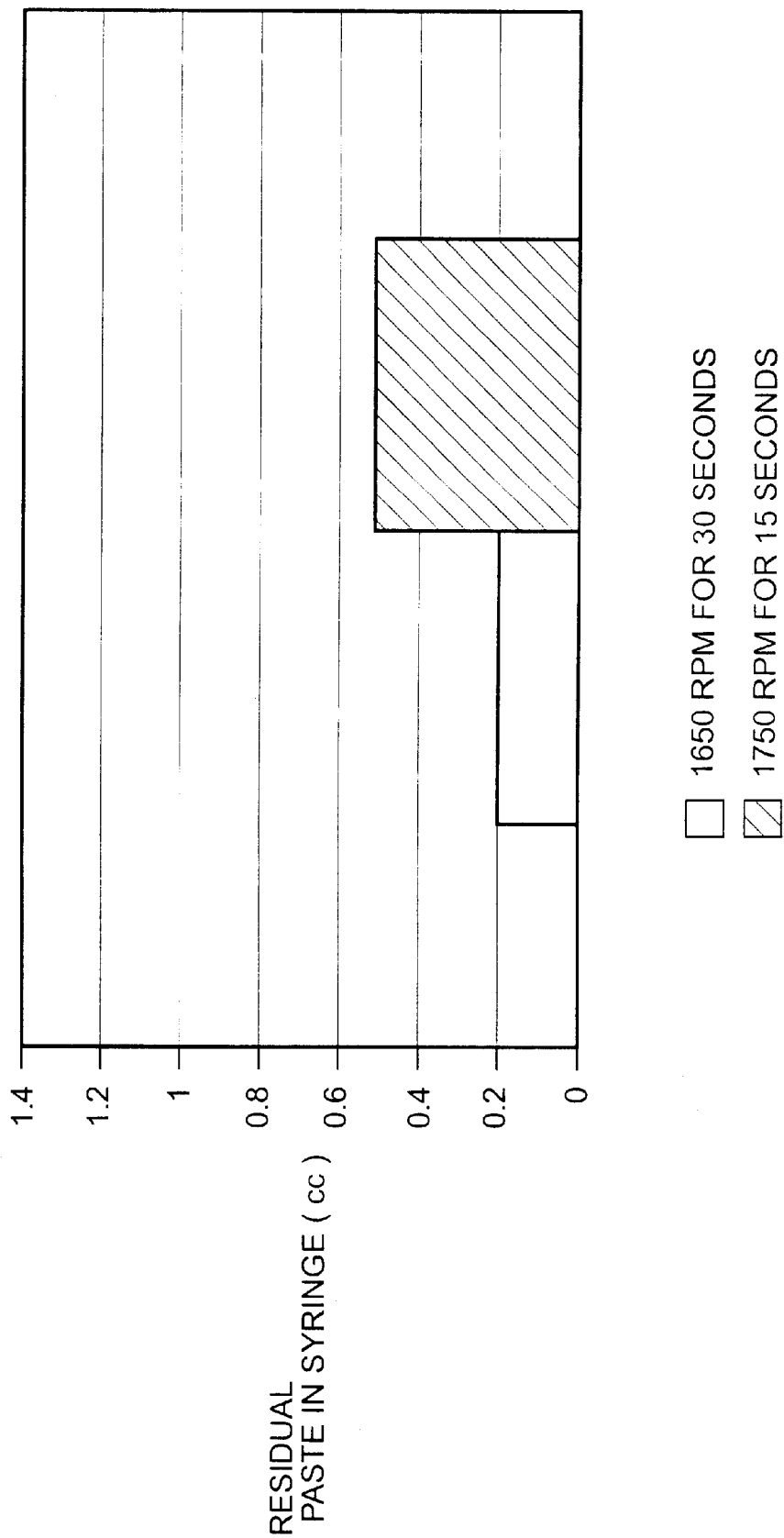
FIG. 10 is a graph representing the residual paste in the syringe in the test apparatus of FIG. 7 with the left column along the x-axis representing mixing at 1650 rpm for 30 seconds and the right graph mixing at 1750 rpm for 15 seconds in the mixer of the present invention.

Both of the values shown in FIG. 9 for residual paste are low compared to slower mixing rates. The two pivot point mixing motion results in slightly better mixing, and subsequent flow out of the needle. Time for complete mixing was evaluated on the two pivot point mixing head as shown in FIG. 10 Again, the vertical y-axis scale is the same as in FIGS. 8 and 9. Thirty seconds of mixing with the mixing apparatus 10 of the present invention results in more complete wetting of the paste and better flow of the paste out of the syringe, even when higher mixing rates are used for a shorter time.

FIG. 11 shows that mixing at a 10% higher speed can have a significant benefit on the flowability of a calcium phosphate bone cement. Again the y-axis indicates residual percentage of paste in cubic centimeters.

At the highest mixing rates, this material had good flow, and could be delivered out of an 18 gauge needle. Again, insufficient energy input in the mixing cycle will result in an inability to get the desired flow characteristics in the paste.

From the above, it is clear that the energy of agitation imparted by mixer 10 of the present invention is critical and must be sufficient to cause substantially complete mixing of the powder and liquid components such that a homogenous mixture or paste is formed. From these tests it has been calculated that this energy input must be at least about $3 \times 10^{-3}$ Joules/second per 3 cc of mixture for at least about thirty (30) seconds (0.09 Joules). Note that 5 g of dry powder mixes to approximately 3 cc of cements. The practical indication that the necessary degree of completeness of combination of components has been accomplished is that within one minute after mixing 5 grams of dry calcium phosphate minerals and an aqueous solution for thirty (30) seconds at 1600 cycles per minute, the resulting cement paste is able to be almost completely expelled (about 90%) from a 10 cc syringe through an 18 gauge needle. Hand mixing or low speed mechanical mixing of the dry and liquid components would only allow partial expulsion (less than 80%) of the resulting paste under these conditions. The cement mixed by hand, that is, at significantly lower energy input than with the mixer of the current invention, will tend to separate back into liquid and powder components under the pressure of trying to expel it through an 18 gauge needle. The liquid component will be preferentially expelled, leaving behind a drier mixture of the cement that, as the situation progresses, will eventually not be able to flow at all.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

What is claimed is:

1. An apparatus for mixing dry and liquid components to form a setting paste comprising:

a holder mounted on said apparatus, said holder mounted for reciprocating movement, said movement having an amplitude with components in at least a first and second direction;

a drive system operatively connected to said holder for imparting said reciprocating movement to said holder at at least 1600 cycles per minute wherein said reciprocating movement occurs in a plane with the at least first and second component directions being perpendicular along said plane, said drive system includes an input shaft rotating a drive plate, said plate having said holder pivotally mounted thereon at a first pivot point offset from an axis of said input shaft to impart an eccentric motion to said holder as said drive plate rotates about said axis, said holder has a first end coupled to said first pivot point and a second end pivotally mounted on said apparatus at a second pivot point in a manner permitting a first amplitude of movement in said first direction and permitting a lower amplitude of movement in said second direction, said apparatus includes a body having said drive plate mounted thereon with said input shaft rotating said plate about said axis and said first holder end pivot point radially spaced from said axis and said second holder end including a pin slidably mounted on a longitudinal slot in said body, said slot extending in said first direction; and a container mounted in said holder having a mass of dry and liquid components therein, said drive system imparting an energy input of at least about $3 \times 10^{-3}$ Joules per second per 3 cc of mixture.

2. The mixing apparatus for mixing as set forth in claim 1 wherein said number of cycles per minute is at least about 1600 and said reciprocating motion is continued for at least 30 seconds.

3. The mixing apparatus as set forth in claim 1 wherein said first holder includes a means for removably mounting said container in said first holder.

4. The mixing apparatus as set forth in claim 1 wherein said container is a syringe containing said dry component and liquid component.

5. The mixing apparatus as set forth in claim 1 wherein said dry component comprises a calcium phosphate mineral powder and said liquid component is an aqueous solution.

6. The mixing apparatus as set forth in claim 5 wherein said calcium phosphate mineral comprises tetra-calcium phosphate and di-calcium phosphate.

7. The mixing apparatus as set forth in claim 6 wherein the aqueous solution contains sodium phosphate.

8. The mixing apparatus as set forth in claim 5 wherein the ratio of liquid to dry powder is between about 0.25 and about 0.30.

9. An apparatus for mixing dry particles of a calcium phosphate mineral powder and an aqueous solution comprising:

a calcium phosphate mineral powder and an aqueous solution;

a body having a reciprocating drive system mounted thereon, said drive system includes an input shaft rotating a drive plate, said drive plate having a holder pivotally mounted thereon at a pivot point offset from an axis of said input shaft to impart an eccentric motion to said holder as said drive plate rotates about said axis, said holder having a first end coupled to said pivot point and a second end mounted on said apparatus in a manner permitting a first amplitude of movement in said first direction and permitting a lower amplitude of movement in said second direction;

a container containing the calcium phosphate mineral powder and the aqueous solution, the container mounted in said holder on said reciprocating drive system, said drive system imparting back and forth movement to said container in at least two directions, said movement at a speed of at least 1600 cycles per minute for a sufficient time to impart an energy input of at least about $3 \times 10^{-3}$ Joules per second per 3 cc of mixture and to completely coat the particles of said calcium phosphate mineral with the aqueous solution.

10. The mixing apparatus as set forth in claim 9 where the ratio of aqueous solution to powder is about 0.25 to about 30.

11. The mixing apparatus as set forth in claim 9 wherein the number of cycles of back and forth motion is at least about 1600 per minute and the time is at least 30 seconds.

12. The mixing apparatus as set forth in claim 9 wherein the powdered calcium phosphate material is tetra-calcium phosphate and di-calcium phosphate.

13. The mixing apparatus as set forth in claim 9 wherein the dry calcium phosphate material includes dry sodium phosphate particles.

14. The mixing apparatus as set forth in claim 9 wherein said apparatus includes a body having said drive plate mounted thereon with said input shaft rotating said plate about said axis and said holder first end pivot point radially spaced from said axis and said holder second end including a pin slidably mounted on a longitudinal slot in said body, said slot extending in said first direction.

15. The mixing apparatus as set forth in claim 9 wherein the amplitude in said first direction is about 3.2 cm.

16. A method for mixing dry calcium phosphate minerals with an aqueous solution comprising:

placing the dry calcium phosphate minerals and the aqueous solution in a container;

mixing the dry calcium phosphate minerals and the aqueous solution by agitating the material in the container at a speed of at least 1600 cycles per second for at least about thirty seconds; said mixing inputting at least about $3 \times 10^{-3}$ Joules of energy per second per 3 cc of mixture are inputted into the mixture during agitation placing 3 cc of the mixture in a syringe having an 18 gauge needle; and expelling the mixture from the syringe through said needle with the test being successful of at least about 90% of the mixture is expelled from said syringe within one minute after the completion of mixing.

17. The method for mixing as set forth in claim 16 wherein the dry calcium phosphate is tetra-calcium phosphate and di-calcium phosphate powder.

18. The method for mixing as set forth in claim 17 wherein the liquid is chosen from the group of a sodium phosphate solution, sterile water, deionized water and a combination thereof.

19. The method for mixing as set forth in claim 16 wherein the container is a syringe.

20. A method for mixing a calcium phosphate bone cement comprising:

placing dry calcium phosphate mineral material and an aqueous solution in a liquid to dry material ratio of 0.25 to 0.30 in a container; and mixing the dry calcium phosphate minerals and the aqueous solution by agitating the container at a speed of at least 1600 cycles per minute to input at least about $3 \times 10^{-3}$ Joules of energy per second per 3 cc of mixture.

21. An apparatus for mixing dry particles of a calcium phosphate mineral powder and an aqueous solution comprising:

a calcium phosphate mineral powder and an aqueous solution;

a body having a reciprocating drive system mounted thereon; and a container containing the calcium phosphate mineral powder and the aqueous solution, the container mounted in a holder on said reciprocating drive system, said drive system imparting back and forth movement to said container in at least two directions, said movement being at least 1600 cycles per minute and at a sufficient amplitude for a sufficient time to completely coat the particles of said calcium phosphate mineral with the aqueous solution by inputting at least about $3 \times 10^{-3}$ Joules of energy per 3 cc of mixture.

22. The mixing apparatus as set forth in claim 21, wherein the ratio of aqueous solution to powder is about 0.25 to about 0.30.

23. The mixing apparatus as set forth in claim 21, wherein the time is at least 30 seconds.

24. The mixing apparatus as set forth in claim 21, wherein the powdered calcium phosphate material is tetra-calcium phosphate and di-calcium phosphate.

25. The mixing apparatus as set forth in claim 21, wherein said drive system includes an input shaft rotating a drive plate, said drive plate having said holder pivotally mounted thereon at a pivot point offset from an axis of said input shaft to impart an eccentric motion to said holder as said drive plate rotates about said axis, said holder having a first end coupled to said pivot point and a second end mounted on said apparatus in a manner permitting a first amplitude of movement in said first direction and permitting a lower amplitude of movement of said second direction.

26. The mixing apparatus as set forth in claim 25, wherein said apparatus includes a body having said drive plate mounted thereon with said input shaft rotating said plate about said axis and said first holder end pivot point radially spaced from said axis and said second holder end including a pin slidably mounted on a longitudinal slot in said body, said slot extending in said first direction.

27. The mixing apparatus as set forth in claim 26, wherein the amplitude in said first direction is about 3.2 cm.

28. The method of mixing as set forth in claim 21, further comprising testing the mixture by placing 3 cc of the mixture in a syringe having an 18 gauge needle and expelling the mixture from the syringe through said needle with the test being successful if at least about 90% of the mixture is expelled from said syringe within one minute after the completion of mixing.

* * * * *